US011008604B2

(12) United States Patent
Lamerton et al.

(10) Patent No.: US 11,008,604 B2
(45) Date of Patent: May 18, 2021

(54) ANALYTE DETECTION ON A SOLID SUPPORT BY NUCLEIC ACID AMPLIFICATION COUPLED TO AN IMMUNOASSAY

(71) Applicant: GE HEALTHCARE UK LIMITED, Little Chalfont (GB)

(72) Inventors: Kathryn Louise Lamerton, Cardiff (GB); Jeffrey Kenneth Horton, Cardiff South (GB); Peter James Tatnell, Cardiff South (GB)

(73) Assignee: Global Life Sciences Solutions Operations UK Ltd, Sheffield (GB)

(*) Notice: Subject to any disclaimer, the term of this patent is extended or adjusted under 35 U.S.C. 154(b) by 5 days.

(21) Appl. No.: 15/529,597

(22) PCT Filed: Dec. 8, 2015

(86) PCT No.: PCT/US2015/064409
§ 371 (c)(1),
(2) Date: May 25, 2017

(87) PCT Pub. No.: WO2016/099999
PCT Pub. Date: Jun. 23, 2016

(65) Prior Publication Data
US 2017/0260566 A1 Sep. 14, 2017

Related U.S. Application Data

(60) Provisional application No. 62/093,530, filed on Dec. 18, 2014.

(51) Int. Cl.
*C12Q 1/68* (2018.01)
*G01N 33/50* (2006.01)
*G01N 33/53* (2006.01)
*C12Q 1/6804* (2018.01)
*G01N 33/543* (2006.01)
*C12Q 1/686* (2018.01)
*C12Q 1/6851* (2018.01)

(52) U.S. Cl.
CPC .......... *C12Q 1/6804* (2013.01); *C12Q 1/686* (2013.01); *C12Q 1/6851* (2013.01); *G01N 33/54306* (2013.01); *C12Q 2525/205* (2013.01); *G01N 2458/10* (2013.01)

(58) Field of Classification Search
CPC .......... C12Q 1/68; G01N 33/53; C07H 21/00
See application file for complete search history.

(56) References Cited

U.S. PATENT DOCUMENTS

| 4,207,307 A * | 6/1980 | Kaul ........ C07K 16/44 436/542 |
| 5,135,874 A * | 8/1992 | Esmon .......... G01N 33/86 435/7.94 |
| 5,281,540 A | 1/1994 | Merkh et al. |
| 5,432,097 A * | 7/1995 | Yourno .................. C12N 1/06 422/504 |
| 5,502,998 A * | 4/1996 | Miller ................. G01N 1/2273 73/1.06 |
| 5,582,705 A * | 12/1996 | Yeung .............. G01N 27/44721 204/452 |
| 5,942,415 A * | 8/1999 | Schraven ............... C07K 14/47 435/252.3 |
| 6,037,465 A * | 3/2000 | Hillebrand ......... C12N 15/1006 435/91.1 |
| 6,900,019 B1 * | 5/2005 | Horton ............... G01N 33/6869 435/174 |
| 8,030,479 B2 * | 10/2011 | Lee .................... C12N 15/1006 536/25.4 |
| 2001/0031469 A1 * | 10/2001 | Volinia ................ C12Q 1/6816 435/6.12 |
| 2002/0013003 A1 * | 1/2002 | Wagner .................. G01N 33/52 436/518 |
| 2002/0115089 A1 * | 8/2002 | Goldstein .......... C12N 15/1006 435/6.11 |

(Continued)

FOREIGN PATENT DOCUMENTS

| CN | 102269759 A | 12/2011 |
| CN | 103698506 A | 4/2014 |

(Continued)

OTHER PUBLICATIONS

Shumaker et al., Human Mutation 7 :346 (Year: 1996).*
Tonkinson et al. ,Frontiers in Bioscience c1-12 Jan. 2002.*
Carpene et al., Metallothionein functions and structural characteristics. J. of Trace Elements in Medicine and Biology21 S135-39 (Year: 2007).*
Chang et al., Effect of Sorbitol and Residual Moisture on the Stability of Lyophilized Antibodies: Implications for the Mechanism of Protein Stabilization in the Solid State. J. of Pharmaceutical Sciences 94(7) : 1445 (Year: 2006).*
Klaster et al., Stabilized, Freeze-Dried PCR Mix for Detection of Mycobacteria. J. of Clinical Microbiology 36(6): 1798 (Year: 1998).*
Kruse et al., Structure of a specific alcohol-binding site defined by the odorant binding protein LUSH from *Drosophila melanogaster*. Nature Structural Biology 10(9) : 694 (Year: 2003).*
Kutateladze et al., Multivalent Mechanism of Membrane Insertion by the FYVE Domain. J. of Biological Chemistry 279 (4): 3050 (Year: 2004).*

(Continued)

*Primary Examiner* — Ethan C Whisenant
(74) *Attorney, Agent, or Firm* — Eversheds Sutherland (US) LLP

(57) ABSTRACT

Embodiments of the invention provides a method for detection of at least one analyte derived from a sample, comprising the steps of: a) depositing the sample on a surface of a solid support; b) transferring at least a portion of the solid support to a receptacle suitable for performing a specific binding assay for one or more analytes of interest; c) optionally washing the portion; d) adding a single specific binding partner for each analyte of interest to the receptacle, the binding partner being labelled with an oligonucleotide sequence; e) mixing the portion with nucleic acid amplification reagents; f) amplifying the oligonucleotide sequence; and g) detecting amplified nucleic acid. The invention also provides a kit for use with the method for detection of at least one analyte derived from a sample.

20 Claims, 3 Drawing Sheets

Specification includes a Sequence Listing.

(56) References Cited

U.S. PATENT DOCUMENTS

| | | | |
|---|---|---|---|
| 2003/0149259 A1* | 8/2003 | Callahan | C12Q 1/701 536/24.32 |
| 2003/0216337 A1* | 11/2003 | Hallahan | A61K 48/0008 514/44 R |
| 2004/0121338 A1* | 6/2004 | Alsmadi | C12Q 1/6844 435/6.12 |
| 2004/0166554 A1* | 8/2004 | Chamoles | C12Q 1/34 435/18 |
| 2004/0175693 A1* | 9/2004 | Lu | C12Q 1/25 435/5 |
| 2004/0215011 A1* | 10/2004 | Deggerdal | C12N 15/1006 536/25.4 |
| 2005/0202573 A1 | 9/2005 | Koyata et al. | |
| 2005/0215924 A1* | 9/2005 | Kao | A61B 10/0045 600/573 |
| 2006/0016747 A1* | 1/2006 | Sakaino | B01D 39/2017 210/450 |
| 2007/0037185 A1* | 2/2007 | Coolbaugh-Murphy | C12Q 1/6827 435/6.11 |
| 2008/0003564 A1* | 1/2008 | Chen | B01L 3/502 435/5 |
| 2008/0305481 A1* | 12/2008 | Whitman | C12Q 1/6818 435/6.12 |
| 2009/0306230 A1* | 12/2009 | Semikhodskii | C12Q 1/6834 514/789 |
| 2010/0291562 A1* | 11/2010 | Adler | C12Q 1/6804 435/6.12 |
| 2011/0269246 A1* | 11/2011 | Oglesbee | G01N 33/6893 436/501 |
| 2012/0003749 A1* | 1/2012 | Yoshida | C07H 21/00 436/501 |
| 2012/0258890 A1 | 10/2012 | Lu et al. | |
| 2013/0210167 A1* | 8/2013 | Benchikh | C07D 405/06 436/501 |
| 2013/0330777 A1* | 12/2013 | Zhang | C12Q 1/6846 435/91.2 |
| 2014/0087363 A1* | 3/2014 | Ruhwald | G01N 33/5695 435/5 |
| 2014/0113294 A1 | 4/2014 | Horton et al. | |
| 2014/0193840 A1 | 7/2014 | Hsu et al. | |
| 2014/0295433 A1 | 10/2014 | Chen et al. | |
| 2016/0047720 A1* | 2/2016 | Wolgast | C12Q 1/6806 506/7 |
| 2016/0223545 A1* | 8/2016 | Kumar | G01N 33/573 |
| 2016/0274130 A1* | 9/2016 | Savjani | G01N 33/6863 |
| 2017/0137874 A1* | 5/2017 | Heller | C12P 19/34 |

FOREIGN PATENT DOCUMENTS

| | | |
|---|---|---|
| JP | 2009-124990 A | 6/2009 |
| WO | 2008/122310 A1 | 10/2008 |
| WO | 2012/113906 A1 | 8/2012 |
| WO | 2012/113911 A1 | 8/2012 |

OTHER PUBLICATIONS

Li et al., Label-free aptamer-based colorimetric detection of mercury ions in aqueous media using unmodified gold nanoparticles as colorimetric probe. Anal. Bioanal. Chem. 393 :2051 (Year: 2009).*

Micic et al., Improved Stability of Apolipoproteins A-I and B in Filter-Paper blood spots impregnated with Ascorbic Acid. Clinical Chemistry 41 (7) : 1042 (Year: 1995).*

Parker et al., The use of dried blood spot sample in epidemiological studies. J. of Clinical Pathology 52 : 633 (Year: 1999).*

Stojanovic et al., Aptamer-Based Colorimetric Probe for Cocaine. JACS 124:9678 (Year: 2002).*

Tebar et al., Clathrin Assembly Lymphoid Myeloid Leukemia (CALM) Protein: Localization in Endocytic-coated Pits, Interactions with Clathrin, and the Impact of Overexpression on Clathrin-mediated Traffic. Molecular Biology of the Cell 10 :2687 (Year: 1999).*

Van Dissel et al., Assessment of the diagnostic potential of immuno-RCA in 96-well ELISA plates for foot-and-mouth disease virus . J. of Virological Methods 147:151-156 (Year: 2008).*

Ng et al. Ann Clin Biochem. 28 : 613 (Year: 1991).*

EP Extended Search Report for EP Application No. 15870700.0 dated Apr. 25, 2018 (9 pages).

Michaud et al., "Long-Term Storage at Tropical Temperature of Dried-Blood Filter Papers for Detection and Genotyping of RNA and DNA Viruses by Direct PCR," Journal of Viorlogical Methods, 2007, 146:257-265.

Nikitina et al., "A New Immuno-PCR Format for Serological Diagnosis of Colon Cancer," Molecular Biology, 2014, 48(1):99-104.

Saravanan et al., "Development of Dot-ELISA for Diagnosis of Peste des petits ruminants (PPR) in Small Ruminants," J. Appl. Anim. Res., 2006, 30:121-124.

PCT International Search Report and Written Opinion for PCT Application No. PCT/US2015/064409 dated Mar. 21, 2016 (8 pages).

European Office Action for EP Application No. 15 870 700.0 dated Jan. 11, 2019 (6 pages).

Japanese Office Action for JP Application No. 2017-530747 dated Aug. 23, 2019 (7 pages with English translation).

Honma et al., "Examination of anti-HIV Antibody Screening for Pregnant Women Using Dried Filter Paper Blood," Sapporo City Research Institute Annual Report 26, 1999, pp. 35-38 (with machine translation).

Fitzgerald et al., "Development of a High-Throughput Automated Analyzer Using Biochip Array Technology," Clinical Chemistry, 2005, 51(7):1165-1176.

Chinese Office Action for CN Application No. 201580069163.8 dated Jun. 19, 2020 (23 pages, with English translation).

Bauler et al., "The FERM and PDZ Domain-Containing Protein Tyrosine Phosphatases, PTPN4 and PTPN3, are both Dispensable for T Cell Receptor Signal Transduction," PLoS ONE, 2008, 3(12):e4014 (11 pages).

Li et al. "Progress in immuno-PCR Research," Foreign Medical Sciences, 1999, (section of Clinical Biochemistry and Laboratory Medicine), 20(5):225-227.

* cited by examiner

1 = 903 Card, 2 = FTA Elute Card, 3 = FTA Gene Card, 4 = FTA Elute Card, washed, 5 = FTA Gene Card, washed, M = Size Marker, - Negative control, + Positive control (purified human genomic DNA).

SEQUENCE LISTING

<160> NUMBER OF SEQ ID NOS: 12

<210> SEQ ID NO 1
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 1
gagaatcgct tgaacccggg aggtgtaggt                        30

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2
cctgctgatg cctggcctct ttcttctttg                        30

<210> SEQ ID NO 3
<211> LENGTH: 30
<212> TYPE: DNA
<213> ORGANISM: Artificial sequence

```
<220> FEATURE:
<223> OTHER INFORMATION: Synthetic oligonucleotide

<400> SEQUENCE: 3
catcagcccg tctaggaacc cagtcatcag                                    30

<210> SEQ ID NO 4
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 4
ctccttcatc ccgctacacc acgcatacac                                    30

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
gcactggctt aggagttgga ct                                            22

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
acagacaccc aggcctactt g                                             21

<210> SEQ ID NO 7
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 7
gcactggctt aggagttgga cttgaaacc                                     29

<210> SEQ ID NO 8
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 8
caactgctga aagagatgcg gtggg                                         25

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: S is G or C.
```

```
<400> SEQUENCE: 9
agcccttggg gasttgaatt gctg                                              24

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (18)..(18)
<223> OTHER INFORMATION: R is A or G.

<400> SEQUENCE: 10
gcactccaga ggacagcrgt gtcaata                                           27

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gcgcacagag gaagagaatc                                                   20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ccaaggcctc attcagctct                                                   20
```

ANALYTE DETECTION ON A SOLID SUPPORT BY NUCLEIC ACID AMPLIFICATION COUPLED TO AN IMMUNOASSAY

CROSS REFERENCE TO RELATED APPLICATIONS

This application claims the priority benefit of PCT/US2015/064409 filed on Dec. 8, 2015 which claims priority benefit of U.S. Provisional Patent Application No. 62/093,530 filed Dec. 18, 2014. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 15, 2017, is named 39154556_1.txt and is 2,850 bytes in size.

FIELD OF THE INVENTION

The present invention relates to a method for detecting at least one analyte derived from a sample. More specifically, the invention relates to an ultrasensitive detection method for an analyte on a solid support, as well as reagent kit for performing the method.

BACKGROUND OF THE INVENTION

Immuno-polymerase chain reaction (iPCR) is a promising technique for the ultrasensitive analysis of proteins and other antigens. It combines the well-established ELISA methodology with the signal amplification power of PCR. iPCR leads to ~1000-to 10,000-fold gain in sensitivity, as compared to conventional ELISA (Adler, M., Wacker, R., & Niemeyer C. M. A real-time immune-PCR assay for routine ultrasensitive quantification of proteins. Biochemical and Biophysical Research Communications (2003) 308, 240-250.) and reveals a very broad linear dynamic range of up to six orders of magnitude. Therefore, the use of immuno-polymerase chain reaction (iPCR) and real-time iPCR assays enable the detection of rare biomarkers in complex biological samples that are poorly accessible by conventional immunoassays.

Conventional ELISA methods have already been used for detection of HIV, HTLV, HCV and many other disease markers from samples applied to 903/Guthrie cards (Parker, S. P. & Cubitt, W. D. J. Clin. Pathol. (1999) 52, 633-639.), for example, the commercially available Human Immunodeficiency Virus Type 1 p24 Antigen ELISA assay has been successfully modified for use on Dried Whole-Blood Spot (i.e., blood applied to 903 paper) eluates and used as a reliable test for infant diagnosis (Patton, J. C., Sherman, G. G., Coovadia, A. H., Stevens, W. S., & Meyers, T. M. Clin. Vaccine. Immunol. (2006), 13 (1), 152-155) Immuno-PCR has been used for many of the same applications as classical ELISA, such as detection of prion, toxins, hormones, pesticides, virus and other antigen. iPCR has been used for the detection of protooncogene ETS1 (Zhou, H., Fisher R. J., & Papas, T. S., Universal immune-PCR for ultra-sensitive target protein detection Nucleic Acids Research, (1993) 21, 6038-6039.), TNF-α(Komatsu, M. et al Tumour necrosis factor-alpha in serum of patients with inflammatory bowel disease as measured by a highly sensitive immune-PCR. Clin. Chem. (2001) 47, 1297-1301.), interleukin-3 and stem cell factor (Putuckova, L. et al Rapid and sensitive detection of cytokines using functionalized gold nanoparticles based immune-PCR, comparison with immuno-PCR and ELISA. J.Immunol. Methods (2011) 37, 38-47; T-cell receptors (Sperl, J. et al Soluble T cell receptors; detection and quantitative assay in fluid phase via ELISA or immune-PCR. J. Immunol. Methods (1995) 186, 181-194.), angiotensinogen (Sugawara, K., et al A highly sensitive immune-polymerase chain reaction assay for human angiotensinogen using the identical first and second polyclonal antibodies. Clin. Chim Acta (2000) 299, 45-54.), protein toxins (He, X. et al Sensitive detection of Shiga toxin 2 and some of its variants in environmental samples by a novel immune-PCR assay. Appl. Environ. Microbiol. (2011) 77, 3558-3564; Zhang, W. et al New immune-PCR assay for detection of low concentrations of Shiga toxin 2 and variants. J. Clin. Microbiol. (2008) 46, 1292-1297.), prion protein (Barletta, J. A. et al Detection of ultra-low levels of pathologic prion protein in scrapie infected hamster brain homogenates using real-time immuno-PCR J. Virol. Methods (2005) 127, 154-164.), potential viral as well as bacterial antigens (Niemeyer, C. M. Adler, M., & Wacker, R. Immuno-PCR: high sensitivity detection of proteins by nucleic acid amplification. Trends Biotechnol. (2005) 3, 208-216; Perez, J. W. et al Detection of respiratory syncytial virus using nanoparticle amplified immuno polymerase chain reaction. Anal. Biochem. (2011) 410,141-148.), mycobacterial RD antigens (Mehta, P. K. et al. Development of an ultrasensitive polymerase chain reaction-amplified immunoassay based on mycobacterial RD antigens: implications for the serodiagnosis of tubercolosis. Diagnostic Microbiology and Infectious Disease (2012) 72, 166-174.) and can be adapted as a novel diagnostic tool for various infectious diseases (Malou, N. & Raoult, D. A promising ultrasensitive diagnostic method to detect antigens and antibodies. Trends Microbiol. (2011) 19, 295-392.).

As an example, iPCR may be used to detect solid-phase immobilized antigen. Traditionally, an ELISA assay using a biotinylated IgG and a streptavidin enzyme conjugate is used to detect solid-phase immobilized antigen. Real-time iPCR may be used as a more sensitive assay, using an antibody—DNA conjugate. To increase the performance of the rt-iPCR assay, an internal competitor DNA fragment can be added to the PCR mixture prior to PCR amplification. Fluorophore-labeled TaqMan probes are added for each DNA to be amplified. During PCR amplification, the TaqMan probe is degraded by the exonuclease activity of the polymerase, thus liberating a fluorescent dye which is quantified in situ by the instrument. As another example, a sandwich iPCR assay, may be applied, e.g., in the detection of rViscumin in human plasma samples using an anti-rViscumin antibody—DNA aggregate. Indirect iPCR assay uses DNA—antibody conjugates with binding specificity for IgG from specific species as secondary reagents for the detection of a primary antibody coupled to the antigen to be detected. For example, DNA—antibody conjugates specific for rabbit-IgG, termed anti-rabbit secondary reagents ("RSR," CHIMERA BIOTEC), were used for the detection of rabbit-IgG, or anti-mouse secondary reagents ("MSR," CHIMERA BIOTEC) for the detection of mouse IgG. (Adler, M., Wacker, R., & Niemeyer C. M. A real-time immune-PCR assay for routine ultrasensitive quantification of proteins. Biochemical and Biophysical Research Communications (2003) 308, 240-250.).

There is a need for applying iPCR and related methods to detect low abundance analyte deposited on a solid support, without the need to separate the analyte from the solid support. The dried format provides enhanced benefits associated with the convenience and stability for storage of a sample in a non-liquid format.

BRIEF SUMMARY OF THE INVENTION

This invention describes a novel method and kit that enables the detection of low abundance analyte from a sample. Thus, in one aspect, it is provided a method for detecting at least one analyte derived from a sample. The method comprises the steps of:
 a) depositing the sample on a surface of a solid support;
 b) transferring at least a portion of the solid support to a receptacle suitable for performing a specific binding assay for one or more analytes of interest;
 c) optionally washing the portion;
 d) adding a single specific binding partner for each analyte of interest to the receptacle, the binding partner being labelled with an oligonucleotide sequence;
 e) mixing the portion with nucleic acid amplification reagents;
 f) amplifying the oligonucleotide sequence ; and
 g) detecting amplified nucleic acid.

In another aspect, the invention provides a kit for performing the novel method. The kit comprises a solid support; a specific binding partner for each analyte of interest, labelled with an oligonucleotide sequence; reagents for amplifying said oligonucleotide sequence; and a user instruction manual.

Further details and advantages of the present invention will appear from the description and claims below.

Figure 1:
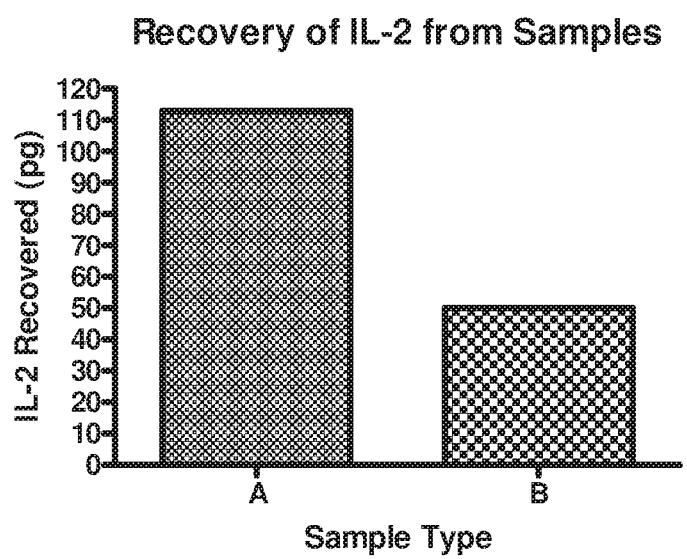
FIG. 1 shows measurement of model protein (IL-2) from a solid support.

DETAILED DESCRIPTION OF THE INVENTION:

In one aspect, the invention provides methods and kits that uses iPCR to detect antibodies or antigens attached to solid supports such as 903 Guthrie cards, 31-ETF paper, FTA or FTA elute. The invention enables diagnosis of body fluids (such as saliva, blood, urine, lymph etc.) or samples used for single cell analysis where, the concentrations are usually too low to detect by current applications. It enables the use of 903 cards (and other solid supports) for diagnosis of diseases that were previously not feasible. The PCR amplification method may also be replaced by isothermal amplification (e.g., such as rolling circle amplification using Phi29 DNA polymerase).

Thus, in one embodiment, it is provided a method for detection of at least one analyte derived from a sample, comprising the steps of:
 a) depositing the sample on a surface of a solid support;
 b) transferring at least a portion of the solid support to a receptacle suitable for performing a specific binding assay for one or more analytes of interest;
 c) optionally washing the portion of transferred solid support;
 d) adding a single specific binding partner for each analyte of interest to the receptacle, which binding partner is labelled with an oligonucleotide sequence;
 e) mixing the portion with nucleic acid amplification reagents;
 f) amplifying the oligonucleotide sequence ; and
 g) detecting amplified nucleic acid.

By the term "analyte", it is meant a substance or chemical constituent that is of interest in an analytical procedure, and is usually detected in a laboratory. An analyte is thus a substance or chemical constituent that is undergoing analysis.

By the term "receptacle", it is meant a hollow object used to contain a portion of the solid support containing the analyte, for the detection of the analyte according to embodiments of the invention. Examples of receptacles are, but not limited to, tubes, test tubes, microtitre plates, cluster wells, dishes, bottles etc. Examples of materials used for the manufacture of receptacles are, but not limited to, glass, plastic, metals, rubber, teflon and polyethylene.

A specific binding assay is a biochemical test that measures the presence or concentration of a molecule, usually in a solution through the use of a specific binding partner, an antibody or immunoglobulin, an aptamer, nucleic acid sequence, ligand or specific binding protein or receptor. The molecule detected by the specific binding assay is often referred to as an analyte. Analytes measured using specific binding assays are frequently used for clinical, research, environmental, forensic and other analytical purposes.

The term "oligonucleotide" refers to single-stranded DNA or RNA molecules, from 15 to 500 nt, preferably 20 -to 400 nt, most preferably 30 to 300 nt in length. For PCR or variations of PCR amplification reactions, the oligonucleotide is linked to the antibody or specific bending moiety and used as a tag or template for amplification. In some other amplification methods, the oligonucleotide can be used as a primer, e.g., in the case of RCA where the antibody is bound to a linear oligonucleotide. A single stranded circular oligonucleotide can then be added (which contains a complimentary sequence to the linear oligonucleotide) which binds to the linear oligonucleotide. The linear oligonucleotide will then be the primer for DNA/RNA replication.

In certain embodiments, the method for detection of at least one analyte derived from a sample further comprises quantifying the analyte of interest based on the quantity of amplified nucleic acid. For example, the amplified nucleic acid may be quantified using a nucleic acid imaging system, or by qPCR/Taqman assay.

In certain embodiments, the solid support comprises: cellulose based paper, woven or non-woven fibrous materials, including man made, or naturally occurring polymer fibres such as an alginate, mineral fibre based materials such as glass fibre materials, or surface treated solid materials for example, chemically or mechanically treated materials, including laser etched surfaces, all provided with a surface micro roughness of sufficient roughness to hold, all optionally chemically treated with a stabilising reagent or reagent mix. The solid support may also be made of nylon or nitrocellulose material.

In certain embodiments, the solid support is fibrous, for example a cellulose fibre material, or a glass fibre/microfibre material.

In certain embodiments, the solid support is a porous polymer, for example porous membrane material such as polyester, polyether sulfone (PES), polyamide (Nylon), polypropylene, polytetrafluoroethylene (PTFE), polycarbonate, cellulose nitrate, cellulose acetate, alginate or aluminium oxide.

In certain other embodiments, the solid support is, but not limited to, FTA paper, FTA Elute paper, Whatman 903 paper, Whatman 31-ETF paper, alginate, or an alginate coated support.

Herein FTA (including FTA microcards, FTA indicating, and FTA classic) is a cellulose fibre paper treated with stabilizing chemicals, for example a weak base, a chelating agent and an anionic surfactant, whereby the support surface is impregnated with the stabilization chemicals. In this way the biological sample materials can be stored as a dried material on the solid support for many months or even years, thereby allowing time for transportation of the solid support, if needed, to a laboratory, at an ambient temperature. Simple recovery is then possible, by for example purifying the biological sample materials from the solid support. Alternatively, the sample can be processed using direct or washed punch-in protocols. Storing a sample on the solid support also enables retesting the sample over time, by removing a portion of the sample and testing that portion as needed.

FTA Elute herein describes similar paper but coated with a chaotropic agent such as guanidinium thiocyanate. Herein Whatman 903 describes uncoated cellulose fibre paper.

In certain embodiments, the solid support surface is impregnated with chemicals, such as a weak base, a chelating agent, an anionic surfactant, and optionally an antioxidant.

In certain embodiments, the solid support surface is impregnated with a chaotrope. In one embodiment, the chaotropic salt is a guanidine salt. In another embodiments, the guanidine salt is selected from the group consisting of guanidine thiocyanate, guanidine chloride and guanidine hydrochloride. In one embodiment, the chaotropic salt is sodium salt such as sodium iodide.

In certain embodiments, the solid support is a cellulose based matrix. In some embodiments, the solid support is a surfactant-treated cellulose based solid support. The term "Surfactants" refers to compounds that lower the surface tension (or interfacial tension) between two liquids or between a liquid and a solid. Surfactants may act as detergents, wetting agents, emulsifiers, foaming agents, and dispersants.

Certain solid supports are described in WO 2012113911, WO 2012113907, WO 2012113906 and WO 2013165870, the disclosure of each is incorporated by reference in its entirety.

The solid supports described above are intended to be used in a generally flat configuration, but in the alternative, may for example be used on a roll.

In certain embodiments, the one or more assays is performed directly from a punch excised from solid support containing the sample. Thus, the assays may be carried out directly from punches excised from solid support on which a sample has been applied. The punches containing the sample may be added directly to an assay reaction. Optionally, simple "punch-ins" additions can be performed in which the excised punch (solid support plus sample) is washed to remove any potential inhibitory chemicals prior to the addition to the reaction.

In certain embodiments, the adding and mixing steps are performed in the presence of a sequestrant to counteract surfactant inhibition of enzyme activity or binding of the specific binding partner. In certain embodiments, the sequestrant is a cyclodextrin. Cyclodextrin acts as a sequestor of detergents which coat the outside of certain solid supports, thus improved DNA amplification and specific binding assays may be performed.

In certain embodiments, the solid support is coated with specific binding moieties, or, surface charge modifying agents. The specific binding moieties are for example antibodies, both polyclonal and monoclonal, specific receptor proteins, ligands, nucleic acid sequences, and similar reagents which, through specific binding or chemical reaction with substances in a specimen, are intended for use for identification, measurement and quantification of an individual chemical substance or analyte in a specimen. The surface charge modifying agents include ion exchange papers such as cationic and anionic charged cellulose papers.

In certain embodiments, the sample is derived from a biological sample. A biological sample (or a biological specimen, also called a bio specimen) is a biological sample including, but not limited to, blood, plasma, serum, cerebral spinal fluid, synovial fluid, lymphatic fluid, saliva, buccal, urine, faeces, skin, hair or tissue. Other biological samples are infectious materials (such as bacteria, viruses, rickettsiae, parasites, or fungi) and those samples obtained from animals.

In certain embodiments, the sample is a drug or derived from the environment such as pollutants, herbicides, pesticides, heavy metals or drugs. By "the environment", it is meant the natural world, as a whole or in a particular geographical area.

In certain embodiments, the sample is derived from a crime scene and is used for forensics purposes such as, but not limited to, blood, semen, hair roots, fibres, alcohol, drug abuse, explosives and gunpowder. By "crime scene" it is meant a location where a crime took place, or another location where evidence of the crime may be found, and comprises the area from which physical evidence is retrieved by law enforcement personnel In certain embodiments, the specific binding partner is an antibody.

In certain other embodiments, the specific binding partner is an aptamer.

In other embodiments, the specific binding partner is a natural or recombinant protein.

In still other embodiments, the specific binding partner is a recombinant Pleckstrin homology domain, FYVE domain, PX domain, ENTH domain, CALM domain, PDZ domains, PTB domains, FERM domain or Metallothioneins. These specific binding partners are all inositide-recognition modules i.e. these are all specific binding partners for inositol phosphates.

In another embodiment, the specific binding partners are members of the clathrin adaptor protein and arrestin families. Clathrin adaptor proteins act as specific binding partners for certain proteins (such as soluble receptors) and lipids, while arrestins are specific binding partners for G-protein coupled receptors.

In yet another embodiment, the specific binding partners are Metallothioneins, a family of cysteine-rich, low molecular weight (MW ranging from 500 to 14000 Da) proteins. Metallothioneins may be used as a specific binding partner for both physiological and heavy metal pollutants. Metallothioneins have the capacity to bind zinc, copper, selenium cadmium, mercury, silver, arsenic, lead, iron metals through the thiol group of the cysteine residues.

The nucleic acid amplification reaction may comprise a polymerase chain reaction. Thus, certain aspects of the invention relates to the application of immune-PCR for a sample deposited on a solid support. As discussed earlier, conventional ELISA methods have already been used for detection of HIV, HTLV, HCV and many other disease markers from samples deposited on a solid support such as 903/Guthrie cards (Parker, S. P. & Cubitt, W. D. J. Clin. Pathol. (1999) 52, 633-639). For example, the commercially available Human Immunodeficiency Virus Type 1 p24 Antigen ELISA assay has been successfully modified for use on Dried Whole-Blood Spot (i.e., blood applied to 903 paper) eluates and used as a reliable test for infant diagnosis (Patton, J. C., Sherman, G. G., Coovadia, A. H., Stevens, W. S., & Meyers, T. M. Clin. Vaccine. Immunol. (2006) 13 (1), 152-155). With the significantly increased sensitivity of immune-PCR, low abundance samples are now successfully detected, using the methods according to certain aspects of the invention.

In certain embodiments, the nucleic acid amplification reaction may comprise an isothermal amplification reaction. The isothermal amplification reaction may comprise rolling circle amplification. When the nucleic acid amplification reaction involves rolling circular amplification, the oligonucleotide may be circularized with T4 ligase, and amplified with Phi 29 DNA polymerase. Alternatively, with the use of circular DNA, the oligonucleotide may act as a primer that hybridizes to the circular DNA, and RCA may proceed in the presence of a Phi29 DNA polymerase.

In certain embodiments, the nucleic acid amplification involves loop mediated isothermal amplification, T7 RNA polymerase, recombinase polymerase amplification or nucleic acid sequence-based amplification In certain embodiments, the method for detecting at least one analyte derived from a sample may further comprise quantifying the analyte of interest based on the quantity of amplified nucleic acid. Methods for quantifying the nucleic acid amplification product are well known. For example, the amplification product may be measured by a hybridisation reaction.

In certain embodiments, the method may be multiplexed. Thus, more than one analytes may be individually detected simultaneously by detecting the amplified nucleic acid sequence associated with each specific binding partner, each labelled with a unique oligonucleotide sequence. A "multiplex assay" or "multiplex method" relates to or is a method of measurement or communication of information or signals from two or more messages from the same source. Simply put, a multiplex assay is a type of assay that simultaneously measures multiple analytes in a single run/cycle of the assay. It is distinguished from procedures that measure one analyte at a time. (An example of a muliplex assay is described by Ugozzoli, et al. (Analytical Biochemistry, 2002, 307, 47-53)).

In certain embodiments, the one or more assays is performed using lyophilized reagents. Lyophilized reagents such as GE Healthcare's *illustra* Ready-To-Go (RTG) products are well known. These reagents may contain the specific binding partner, and/or reagents for analysing the specific oligonucleotides etc.

In certain embodiments, the sample is previously preserved on a solid support and stored at room temperature. The sample may simply be applied to the solid support and allowed to dry at ambient temperature for preservation. Biological sample preserved on a solid support may be stable for a long period of time, see for example, GE Healthcare Life Sciences Application Note 29-0082-33 AA. Thus, the sample may be stored on the solid support for at least 30 minute. The sample may be immobilised on the solid support for longer periods, for example, for at least 24 hours, for at least 7 days, for at least 30 days, for at least 90 days, for at least 180 days, for at least one year, and for at least 10 years. In this way the sample may be stored in a dried form which is suitable for subsequent analysis. Typically, samples are stored at temperatures from −200° C. to 40° C. In addition, stored samples may be optionally stored in dry or desiccated conditions or under inert atmospheres.

The power of iPCR allows for ultrasensitive detection of antibodies or antigens from a sample deposited on a solid support material, which brings a new tool in detecting microbiological disease especially for viral infections or for fastidious bacteria that are difficult to isolate. This methodology also contributes significantly for serological diagnosis of some bacterial or viral diseases such as rickettsia or cytomegalovirus infection, where classical serological methods fail to detect antibodies at early stages of infection and where seroconversion is detected after a few weeks.

In another aspect, the invention provides a kit for performing the method for detection of at least one analyte derived from a sample. The kit comprises a solid support; a specific binding partner for each analyte of interest, labelled with an oligonucleotide sequence; reagents for amplifying the oligonucleotide sequence; and a user instruction manual.

In certain embodiments, the kit also comprises a receptacle suitable for performing a specific binding assay for one or more analytes of interest.

In certain embodiments, the specific binding partners or the reagents for amplifying said oligonucleotide sequence in the kit are provided in ambient temperature stable, dried form.

EXAMPLES

The following examples are intended only to illustrate methods and embodiments in accordance with the invention, and as such should not be construed as imposing limitations upon the claims.

Example 1

Direct Measurement of Interleukin from a Solid Support

Recombinant IL-2±carrier (R & D Systems; Cat. 202-IL-CF-10 µg; lot AE4309112 and Cat. 202-IL-10µg; lot AE4309081 respectively) was dissolved in blood (TCS Biosciences) at 50 pg or 100 pg/µl. Aliquots (1 µl containing, 50 (B) or 100 (A) pg of IL-2) were applied to GE Healthcare 903 filter papers.

These samples were allowed to dry overnight at ambient temperature and humidity. 3mm diameter punched disks were extracted from each paper type using the appropriately sized punch. Single discs were directly analysed for IL-2 with reagents from a fully configured IL-2 Quantikine ELISA kit (R & D Systems, Cat. D2050, lot 273275). Direct assays were carried out "punch in well", i.e., where a portion of the 903 filter paper was punched out and deposited in a reaction well of a convention multiwall plate.

On completion of the assay the optical density was monitored at 450 nm. The recovery of IL-2 was determined by comparing values to a standard curve of known IL-2 concentrations. Recovery rates are shown in FIG. 1, and demonstrate that effective amounts of a protein can be recovered when the protein is deposited on a solid support.

Thus, a protein from a biological sample such as blood or cerebral spinal fluid is stable on a solid support and may be detected and quantified using immunology methods such as ELISA.

Example 2

Direct PCR from Blood Preserved on Whatman FTA and 903 Cards

Thermo Scientific Phusion Blood Direct PCR Kit was demonstrated to support the amplification of DNA directly from blood samples stored on a range of solid supports including Whatman 903, FTA and FTA Elute cards (Chum and Andre 2013; Thermo Fisher Scientific). FTA and FTA elute cards are examples of chemical coated paper-based cards whilst 903 cards are not chemically coated. In direct amplification workflows, no prior DNA extraction or purification steps are needed and the cards are simply added to the PCR reaction mixture.

Sample preparation: Fresh blood or blood preserved with heparin (1.4 IU/mL), $K_2EDTA$ (1.8 mg/mL), or Na Citrate (109 mM) was applied to Whatman 903 Cards, FTA Elute Cards, or FTA Gene Cards and dried as per the manufacturer's instructions. For direct PCR, a 1 mm diameter disc was punched out of the sample in the card and used in the following PCR reaction volumes: Whatman 903: 10-50 µl, FTA Elute Card: 25-50 µl and FTA Gene Card: 50 µl.

When larger punches or smaller reaction volumes were used, punches were washed with 20 µL of water at 50° C. for 3 minutes. After removing the water, PCR components were added directly to the rinsed punch. The parameters and reagents used are listed in Tables 1, 2, 3 below.

TABLE 1

PCR REACTION MIXTURES

| COMPONENT | 25 µL REACTION | 50 µL REACTION | FINAL CONC. |
|---|---|---|---|
| $H_2O$ | ADD TO 25 µL | ADD TO 50 µL | |
| 2x PHUSION BLOOD PCR BUFFER | 12.5 µL | 25 µL | 1x |
| PRIMER F (FORWARD) | x µL | x µL | 0.5 µL |
| PRIMER R (REVERSE) | x µL | x µL | 0.5 µL |
| PHUSION BLOOD DNA POLYMERASE | 0.5 µL | 1 µL | |
| 903/FTA CARD | 1 mm PUNCH | 1 mm PUNCH | |
| OPTIONAL COMPONENTS FOR REACTION OPTIMIZATION* | | | |
| 50 mM $MgCl_2$ | 0.75 µL | 1.5 µL | |
| 50 mM EDTA | 0.6-1.25 µL | 1.25-2.5 µL | |
| DMSO | 1.25 µL | 2.5 µL | 5% |

TABLE 2

PCR THERMO-CYCLING PROTOCOLS. THE 2-STEP PROTOCOL WAS USED WHEN PRIMER Tm VALUES WERE 69-72° C.

| | 2-STEP PROTOCOL | | 3-STEP PROTOCOL | | |
|---|---|---|---|---|---|
| CYCLE STEP | TEMP. | TIME | TEMP. | TIME | CYCLES |
| LYSIS OF CELLS | 98° C. | 5 MINUTE | 98° C. | 5 MINUTE | 1 |
| DENATURATION | 98° C. | 1 s | 98° C. | 1 s | 35-40 |
| ANNEALING* | — | — | x° C. | 5 s | |
| EXTENSION** | 72° C. | 15-30 s/kb | 72° C. | 15-30 s/kb | |
| FINAL EXTENSION | 72° C. | 1 MINUTE | 72° C. | 1 MINUTE | 1 |
| | 4° C. | HOLD | 4° C. | HOLD | |

TABLE 3

PRIMERS USED TO AMPLIFY THE EXEMPLARY GENES OF INTEREST

| GENE OF INTEREST | AMPLICON LENGTH (kb) | FORWARD PRIMER REVERSE PRIMER | ANNEALING TEMPERATURE (° C.) |
|---|---|---|---|
| CATHEPSIN K GENE | 0.5 | GAGAATCGCTTGAAC CCGGGAGGTGTAGGT | 78.1 |
| | | CCTGCTGATGCCTGG CCTCTTTCTTCTTTG | 78.1 |
| GLUTATHIONE PEROXIDASE 3 | 1.0 | CATCACCCGTCTAGG AACCCAGTCATCAG | 77.6 |
| | | CTCCTTCATCCCGCT ACACCACGCATACAC | 77.9 |
| BETA-GLOBIN GENE | 3.8 | GCACTGGCTTAGGAG TTGGACT | 65.9 |
| | | ACAGACACCCAGGCC TACTTG | 65.6 |
| BETA-GLOBIN GENE | 7.5 | GCACTGGCTTAGGAG TTGGACTTCAAACC | 73.9 |
| | | CAACTGCTGAAAGAG ATGCGGTGGG | 75.1 |
| SOX21 GENE 5' REGION (CONTROL PRIMERS OF PHUSION BLOOD DIRECT PCR KIT | 0.2 | AGCCCTTGGGGASTT GAATTGCTG | 73.5 |
| | | GCACTCCAGAGGACA GCRGTGTCAATA | 72.2/75.3 (R = A/G) |

Figure 2:
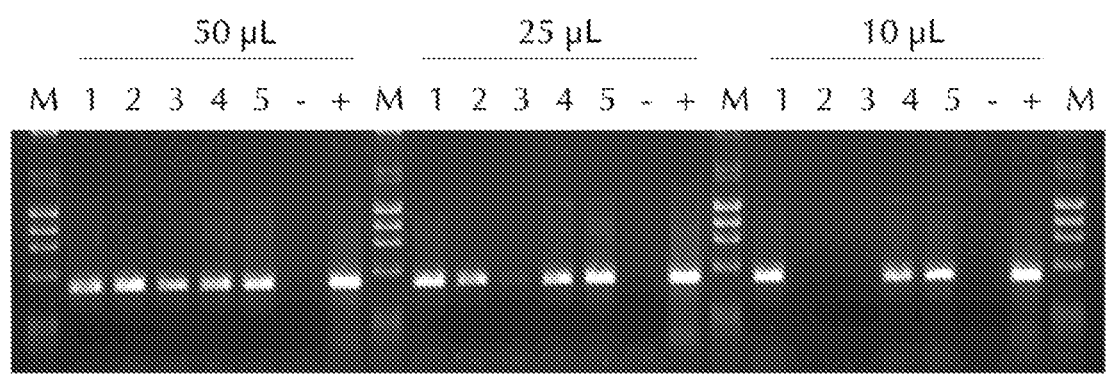
FIG. 2 shows result of direct amplification of a 500 bp genomic DNA fragment from human blood treated with heparin and preserved on various solid supports.

FIG. 2 shows result of direct amplification of a 500 bp genomic DNA fragment from human blood treated with heparin and preserved on various cards. Reactions were performed from 1 mm punches either rinsed or placed directly into PCR reactions of 50, 25 or 10 µl in volume. A 2-step PCR protocol described was used.

Figure 3:
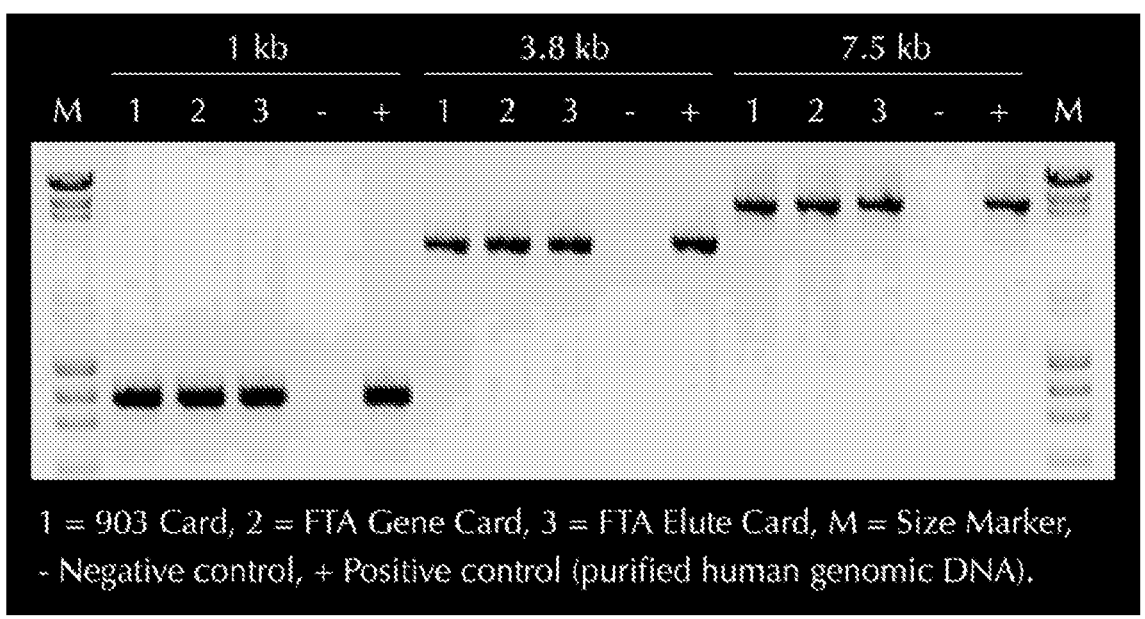
FIG. 3 shows result of direct PCR of 1 kb, 3.8 kb and 7.5 kb genomic DNA amplicons from human blood treated with EDTA and preserved on various solid supports.

FIG. 3 shows result of direct PCR of 1 kb, 3.8 kb and 7.5 kb gDNA amplicons from human blood treated with EDTA and preserved on various cards. Reactions were performed from 1 mm punches in 50 µl reactions (FTA Gene Card punches were washed by rinsing with water for 7.5 kb fragment). A 2-step protocol was used for 1 kb and 7.5 kb fragments and a 3-step protocol for 3.8 kb amplicon.

The PCR study confirmed that DNA can be directly amplified from blood stored on various filter cards.

Samples derived from the 903 Cards showed almost no inhibition, and a 1 mm punch could be used with reaction volumes as low as 10 µl. FTA Elute and FTA Cards exhibited varying levels of inhibition. FTA elute inhibited direct PCR reactions slightly; a 1 mm disc in a 25-50 µl reaction worked well, but when placed in a 10 µl reaction, the PCR was totally inhibited. FTA Gene Cards showed the greatest level of inhibition. Without any pre-treatments, a 1 mm punch of FTA Gene Card worked well only in a 50 µl reaction volume. For smaller reaction volumes, a very simple washing protocol was enough to remove inhibitors from both FTA Elute and FTA Gene Cards. After washing the card punch for 3 minutes with water, the sample was of sufficient purity for use in direct PCR reactions with Phusion Blood Direct PCR Kit at all reaction volumes tested.

Punches from 903 Cards and rinsed punches from FTA Elute and FTA Gene Cards (all 1 mm in diameter) were used in 50 pl reaction volumes with primers specific for 1 kb, 3.8 kb and 7.5 kb amplicons. In all cases, the PCR reaction generated the appropriately sized amplification product.

Example of iPCR on a Solid Support

Recombinant human IL-2 was diluted with MADB buffer (150 mM NaCl, 20 mM Tris-HCl pH 7.4 2M guanidine) and added to the solid support overnight at 4° C. This simple addition was sufficient to permanently attach the antigen to the solid support. The immobilised antigen was washed three times with Tris buffered saline (TBS) and non-specific binding site on the solid support were blocked using MESTBS (TBS supplemented with 4.5% non-fat dried milk, 0.1 mM EDTA, 1 mg/ml salmon sperm DNA and 0.2% sodium azide) at 37° C. for 1 hour. The solid support was washed 3 times with TETBS (TBS supplemented with 0.04% Tween and 0.1 mM EDTA). All subsequent washing steps followed this procedure.

Multiple punches were excised from the solid support using a disposable Harris 3 mm Uni-core punch and then added to a 96-well plate suitable for PCR.

Biotinylated goat anti-IL-2 (R&D Systems, catalogue code BAF202) was diluted with reagent dilution buffer (RDB) composed of 1 part of MESTBS plus nine parts of TETBS and was added to the 96-well plate containing the solid support punches. The IL-2 antigen and biotinylated antibody was incubated for one hour at room temperature (22° C.) followed by a three-minute washing step using TETBS. Washing was repeated 5 times.

A 1038 bp fragment of the p53 mRNA co-corresponding to 217-1255 of the p53 cDNA as described in GenBank accession number BC003596 (IMAGE; 3544714, MGC; 646) was used as the template for the immuno-PCR reaction. The appropriate sized p53 DNA fragment was excised from the vector and biotinylated using the random prime DNA biotinylation kit (KPL, catalogue code 60-01-00) using exo-minus fragment of Klenow DNA polymerase using biotin d-CTP.

Free streptavidin (Sigma Catalogue code 54762) was used to link the biotinylated antibody to the biotinylated P53 fragment.

The iPCR detection reaction involved the generation of a 250 bp PCR product using the p53-specific forward primer 1; 5'-GCGCACAGAGGAAGAGAATC-3' and reverse primer 2; 5'-CCAAGGCCTCATTCAGCTCT-3 (Sigma Genosys).

PCR amplicons were generated using a PCR master mix (95 µl; 1 U Taq DNA polymerase, 20 pmol forward and reverse primers) and amplified accordingly (denature 94° C., 3 min. 30 cycles of 94° C., 30 s; 55° C., 1 min; 72° C., 2 min; final soak at 72° C., 10 min).

The resultant amplicons were visualized on a 1% agarose gel (data not shown).

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method for detection of at least one analyte derived from a sample, comprising the steps of:
   a) depositing the sample on a surface of a solid support, drying the sample on the surface of the solid support, and storing the dried sample on the solid support at ambient temperature for at least one month;
   b) transferring at least a portion of the solid support and the dried sample to a receptacle suitable for performing a specific binding assay for one or more analytes of interest;
   c) washing the said portion for at least 3 minutes;
   d) adding a single specific binding partner for each analyte of interest to said receptacle said binding partner being labelled with an oligonucleotide sequence;
   e) mixing said portion with nucleic acid amplification reagents;
   f) amplifying the oligonucleotide sequence; and
   g) detecting amplified nucleic acid,
   wherein the solid support comprises cellulose based paper, or woven or non-woven fibrous materials,
   wherein more than one analytes are individually detected simultaneously by detecting the amplified nucleic acid sequence associated with each specific binding partner, each labelled with a unique oligonucleotide sequence, and
   wherein the binding partners and the nucleic acid amplification reagents are provided in ambient temperature stable, dried form.

2. The method of claim 1, further comprising:
   quantifying the analyte of interest based on the quantity of amplified nucleic acid.

3. The method of claim 1, wherein the solid support comprises man made, or naturally occurring polymer fibres, or mineral fibre based materials all provided with a surface micro roughness of sufficient roughness to be held with a holder.

4. The method of claim 1, wherein the solid support surface is impregnated with at least one of a weak base, a chelating agent, an anionic surfactant, or an anti-oxidant.

5. The method of claim 1, wherein the solid support surface is impregnated with a chaotrope.

6. The method of claim 1, wherein the solid support is a surfactant-treated cellulose based solid support.

7. The method of claim 1, wherein the adding and mixing steps are performed in the presence of a sequestrant to counteract surfactant inhibition of enzyme activity or binding of the specific binding partner.

8. The method of claim 7, wherein the sequestrant is a cyclodextrin.

9. The method of claim 1, wherein the solid support is coated with specific binding moieties, or, surface charge modifying agents.

10. The method of claim 1, wherein the specific binding partner is an antibody.

11. The method of claim 1, wherein the specific binding partner is an aptamer.

12. The method of claim 1, wherein the specific binding partner is a natural or recombinant protein.

13. The method of claim 1, wherein the specific binding partner is a recombinant Pleckstrin homology domain, FYVE domain, PX domain, ENTH domain, CALM domain, PDZ domains, PTB domains, FERM domain or Metallothioneins.

14. The method of claim 1, wherein the sample is derived from a biological sample.

15. The method according to claim 1, wherein the sample comprises one or more of a drug, pollutants, herbicides, pesticides, or metals.

16. The method of claim 1, wherein the sample is derived from a crime scene, wherein the sample comprises blood, semen, hair roots, fibres, alcohol, drugs of abuse, explosives or gunpowder, and wherein the sample is configured to be used for forensics purposes.

17. The method of claim 1, wherein the nucleic acid amplification reaction comprises polymerase chain reaction.

18. The method of claim 1, wherein the nucleic acid amplification reaction comprises isothermal amplification.

19. The method of claim 18 wherein the isothermal amplification reaction comprises rolling circle amplification.

20. The method of claim 19, wherein the amplification product is measured by a hybridisation reaction.

* * * * *